United States Patent [19]
Bender et al.

[11] Patent Number: 5,955,357
[45] Date of Patent: Sep. 21, 1999

[54] IN-VITRO-DERIVED HUMAN NEUTROPHIL PRECURSOR CELLS

[75] Inventors: James G. Bender, Lindenhurst; Phillip B. Maples, Waukegan; Stephen L. Smith, Arlington Heights; Kristen L. Unverzagt, Palatine; Dennis E. Van Epps, Cary, all of Ill.

[73] Assignee: Nexell Therapeutics Inc., Irvine, Calif.

[21] Appl. No.: 08/295,501

[22] Filed: Aug. 23, 1994

Related U.S. Application Data

[63] Continuation-in-part of application No. 07/855,295, Mar. 23, 1992, abandoned.

[51] Int. Cl.$^6$ ................................................. C12N 5/08
[52] U.S. Cl. ............................................................. 435/325
[58] Field of Search ............................. 435/240.1, 240.2, 435/240.21, 240.3, 172.3, 325, 1.1; 424/93.21

[56] References Cited

U.S. PATENT DOCUMENTS

| | | | |
|---|---|---|---|
| 4,714,680 | 12/1987 | Civin | 437/31 |
| 4,965,204 | 10/1990 | Civin | 530/388.7 |
| 5,004,681 | 4/1991 | Boyse et al. | 435/2 |
| 5,061,620 | 10/1991 | Tsukamoto et al. | 435/7.21 |
| 5,079,228 | 1/1992 | Cohen et al. | 362/263 |
| 5,087,570 | 2/1992 | Weissman et al. | 424/93.7 |
| 5,199,942 | 4/1993 | Gillis | 604/4 |
| 5,670,147 | 9/1997 | Emerson et al. | 424/93.1 |
| 5,670,351 | 9/1997 | Emerson et al. | 435/172.3 |

OTHER PUBLICATIONS

Egeland et al., "Myeloid Differentiation of Purified CD34$^+$ Cells After Stimulation With Recombinant Human Granulocyte–Monocyte Colony–Stimulating Factor (CSF), Granulocyte–CSF, Monocyte–CSF, and Interleukin–3," *Blood* 78:3192–3199 (1991).

"Identification and Comparison of CD34–Positive Cells and Their Subpopulations from Normal Perifpheral Blood and Bone Marrow Using Multicolor Flow Cytometry", Bender et al., *Blood* 77, No. 12 1991 pp. 2591–2596.

"Role of c–kit Ligand in the Expansion of Human Hematopoietic Progenitor Cells", Brandt et al., *Blood*, 79, No. 3 1992 pp. 634–641.

"Prophylaxis and Treatment of Infection of the Immunocompromised Host by Granulocyte Transfusions", Buckner et al., *Clinics in Haematology*, vol. 13, No. 3 Oct. 1984 pp. 557–572.

"Granulocyte Transfusions", Clift et al., *The American Journal of Medicine*, vol. 76,pp. 631–636 Apr. 1984.

"Recovery of CFU–GM from Cryopreserved Marrow and in vivo Evaluation after Autologous Bone Marrow Transplantation Are Predictive of Engraftment", Douay et al. *Exp. Hematol.* 14:358–365 (1986).

"Enhanced Reconstitution of Hematopoietic Organs in Irradiated Mice, Following Their Transplantation with Bone Marrow Cells Pretreated with Recombinant Interleukin 3", Fabian et al. *Exp. Hematol.* 15:1140–1144 (1987).

"Studies of the Function and Structure of In Vitro Propagated Human Granulocytes", Frenck, et al. *Pediatric Research* vol. 30, No. 1991, pp. 135–140.

"Early Lympho–Hemopoietic Recovery After Autografting Using Peripheral Blood Stem Cells in Acute Non–Lymphoblastic Leukemia", Juttner, et al. *Transplantation Proceedings*, vol. XX, No. 1, 40–43 Feb. 1988.

"In Vitro Treatment of Peripheral Blood Stem Cells to Increase Committed Progenitor Content", Lasky et al., *Exp. Hematol.* vol. 17, Abstract No. 239, 587 (1989).

"Human Fibroblasts Maintain the Viability and Augment the Functional Response of Human Neutrophils in Culture", Ling et al. *J. Clin. Invest.* vol. 85, Feb. 1990, pp. 601–604.

"Recombinant Human Granulocyte–Macrophage Colony–stimulating Factor Stimulates In Vitro Mature Human Neutrophil and Eosinophil Function, Surface Receptor Expression, and Survival", Lopez et al. *J. Clin. Invest.* vol. 78, Nov. 1986 pp. 1220–1228.

"Granulocyte Transfusions in Neutropenic Patients", Menitove et al. *CRC Critical Reviews in Oncology/Hematology*, vol. 7, Issue 1, 89–113, 1987.

"In Vitro Expansion of the Murine Pluripotent Hemapoietic Stem Cell opulation in Response to Interleukin 3 and Interleukin 6", Okano et al., *Transplantation*, vol. 48, No. 3 495–498 Sep. 1989.

"Expansion of Hematopoietic Progenitor Cells (Pre–CFU) in Serum–Free Culture: Modulation by Cytokines and Stromal Elements", Ottmann et al., *Exp. Hematol.*, vol. 17, Abstract No. 240, 587 (1989).

"Effects of Recombinant Human Interleukin–3 on CD34–Enriched Normal Hematopoietic Progenitors and on Myeloblastic Leukemia Cells", Saeland et al., *Blood* vol. 72, No. 5, 1580–1588, Nov. 1988.

"Combined and Sequential Effects of Human IL–3 and GM–CSF on the Proliferation of CD34+ Hematopoietic Cells From Cord Blood", Saeland et al., *Blood* vol. 73, No. 5, 1195–1201. Apr. 1989.

"A Liquid Culture Method for the In Vitro Growth of Hemopoietic Progenitor Cells . . . Allowing for anallysis by Multiparameter Flow–cytometry", Serke et al., *Eur. J. Haemotol.* 46:85–92 (1991).

"Granulocyte Colony–Stimulating Factor (G–CSF) in Peripheral Blood Stem Cell (PBSC) and Bone Marrow (BM) Transplantation", Sheridan et al., *Blood*, vol. 76, Supp II, Abstract No. 2251, 565a (1990).

(List continued on next page.)

*Primary Examiner*—James Martinell
*Attorney, Agent, or Firm*—Campbell & Flores LLP

[57] ABSTRACT

The present invention provides a composition of human neutrophil precursor cells having at least 37% myeloblasts and promyeloblasts. Also provided are hematopoietic cell suspensions that have human neutrophil precursor cells and at least one hematopoietic growth factor.

30 Claims, 6 Drawing Sheets

OTHER PUBLICATIONS

"The Use of Recombinant Cytokines for Enhancing Immunohematopoietic Reconstitution Following BMT. I. Effect of in vitro Culturing with IL–3 and GM–CSF on human and Mouse BM cells Purged with Mafosfamide (ASTA–Z)", Slavin, S. et al. *Bone Marrow Transplantation* (1989), 4:459–464.

"The Myeloid Progenitor Cell—Its Value in Predicting Hematopietic Recovery After Autologous Bone Marrow Transplantation", Spitzer et al., *Blood* vol. 55, No. 2, 317–323. Feb. 1980.

"Selection of Normal Human Hematopoietic Stem Cells for BMT Using Immunomagnetic Microspheres and CD34 Antibody", Strauss et al., *The Amer. Jour. of Pediatric Hematology/Oncology,* 13(2): 217–221, (1991).

"Enhancement of the Grafting Efficiency of Transplanted Marrow Cells by Preincubation with Interleukin–3 and Granulocyte–Macrophage Colony–Stimulating Factor", Tavassoli et al., *Blood,* vol. 77, No. 7, 1599–1606, (1991).

"Differentiation and Maturation of Growth Factor Expanded Early Human Hematopoietic Progenitors Assessed by Multidimensional Flow Cytometry", Terstappen et al., *Blood,* vol. 78, No. 10, Supp. I, Abstract No. 1182, 298a.

"Flow Cytometric Analysis of Human Bone Marrow. III. Neutrophil Maturation", Terstappen et al., *Leukemia,* vol. 4, No. 9, 657–663. Sep. 1990.

"Selective Multiplication of Hematopoietic Stem Cells for Bone Marrow Transplantation in Mice and Rhesus Monkeys", G. Wagemaker, *Transplantation Proceedings,* vol. XIX, No. 1, 2721–2725, Feb. 1987.

"Leukocyte Transfusions: Think Twice", Wright, *The American Journal of Medicine,* vol. 76, 637–644, Apr. 1984.

"Single Donor Granulocytes and Platelets", Robinson, E.A., *Clinics in Haematology* vol. 13, No. 1, Feb. 1984.

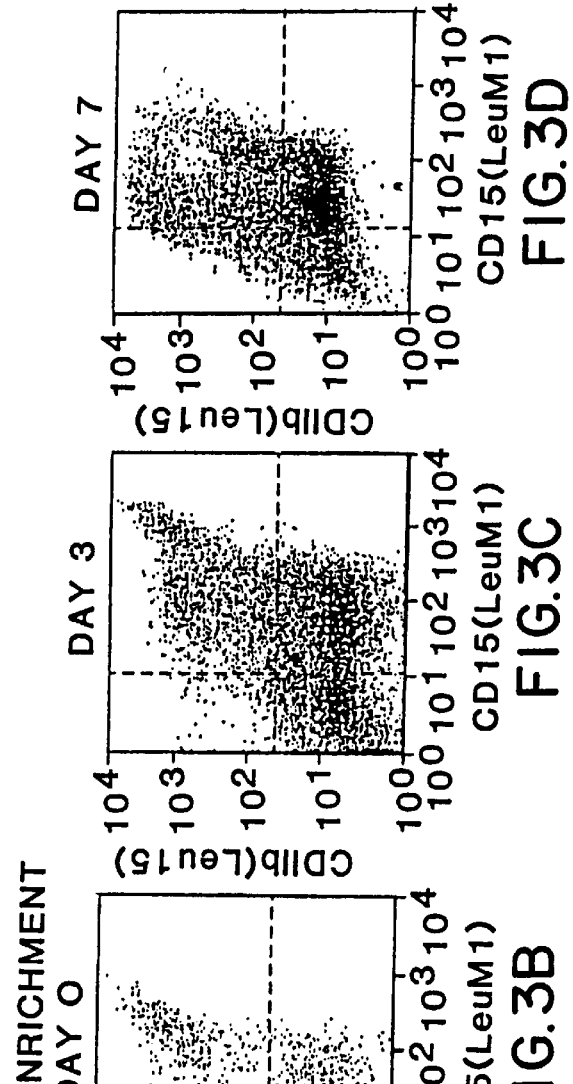
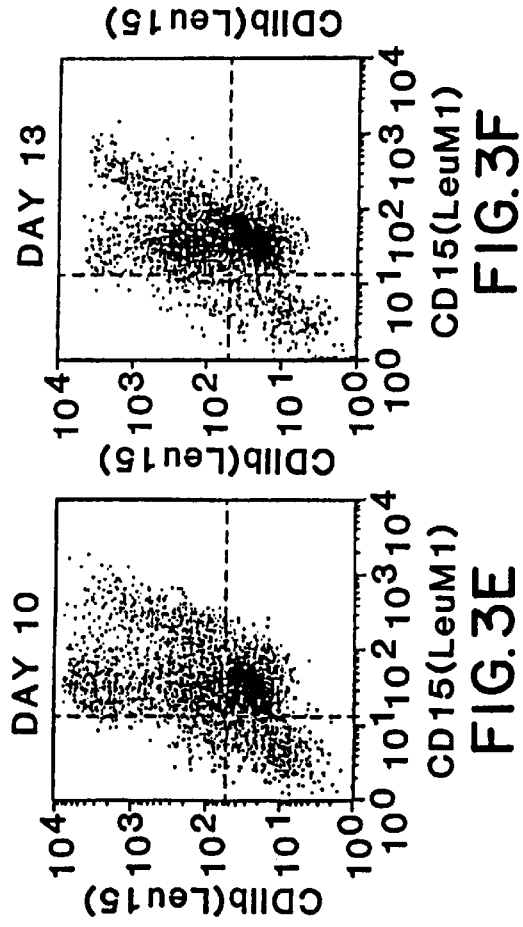

IN-VITRO-DERIVED HUMAN NEUTROPHIL PRECURSOR CELLS

This application is a continuation-in-part of U.S. Ser. No. 07/855,295, filed Mar. 23, 1992, now abandoned, the contents of which are hereby incorporated by reference into the present disclosure.

TECHNICAL FIELD OF THE INVENTION

The present invention relates to an in vitro-derived population of human neutrophil precursor cells and to the use of this population of cells in clinical and research applications.

BACKGROUND OF THE INVENTION

The main infection and disease-fighting cell of the human immune system is the white blood cell (leukocyte), which circulates through the blood. Approximately 50 to 65 percent of all leukocytes are a type of cell called a "neutrophil," which mediates much of the infection-fighting capability of the white cells. When a human has a substantially lower than normal number of circulating neutrophils, the patient is considered to be suffering from "neutropenia," i.e., a condition characterized by an abnormally low number of circulating neutrophils.

A patient suffering from neutropenia then is at substantial risk of infection and disease, as the diminished number of neutrophils circulating in the blood substantially impairs the ability of the patient to fight any infection or disease, as less neutrophils are available to engage in the battle. In severe cases of neutropenia there may be essentially no neutrophils available to fight infection and disease.

Neutropenia, itself, may be the result of disease, genetic disorders, drugs, toxins, and radiation as well as many therapeutic treatments, such as high dose chemotherapy (HDC) and conventional oncology therapy. For example, many cancers have been found to be sensitive to extremely high doses of radiation or anti-neoplastic (anti-cancer) drugs. These cancers include malignant melanoma, carcinomas of the stomach, ovary, and breast, small cell carcinoma of the lung, and malignant tumors of childhood (including retinoblastoma and testicular carcinoma), as well as certain brain tumors, particularly glioblastoma. However, such intensive HDC is not widely used because it frequently causes such a compromise of the hematopoietic system that the result is death due to any of numerous opportunistic infections.

The reason behind the compromise, if not devastation, of the hematopoietic system resulting from HDC is generally understood. The HDC acts upon rapidly proliferating cells in the bone marrow that produce neutrophils, platelets, erythrocytes, lymphocytes, and other leukocytes. When the hematopoietic system is functioning correctly, platelets and neutrophils proliferate rapidly and turn over at a high rate, unlike the lymphocytes and red blood cells, which are long-lived. The result of HDC, then, is that not only are cancerous (neoplastic) cells destroyed, so are the cells of the hematopoietic system that are responsible for generating the army of neutrophils that are necessary to maintain a functioning immune system. Complete destruction of neutrophil progenitor and precursor cells eliminates the patient's short-term capacity to generate mature neutrophils, thereby severely compromising the patient's ability to combat infection. The patient then becomes "immunocompromised" and subject to opportunistic infection. Such a condition may ultimately result in morbidity and death. Other situations also may be encountered where there has been a severe insult to the hematopoietic system, resulting in a substantial reduction in neutrophils and precursors thereto.

In order to understand the problems presented by neutropenia, whether caused by HDC or otherwise, it is first necessary to understand some basic principles about human blood cells, including their source and their development.

Hematopoiesis refers to the proliferation and differentiation of blood cells. The major site of hematopoiesis in humans, after about 20 weeks of fetal life, is the bone marrow. Blood cells develop from multipotent stem cells that are usually located in the bone marrow. These stem cells have the capacity to proliferate and differentiate. Proliferation maintains the stem cell population, whereas differentiation results in the formation of various types of mature blood cells that are grouped into one of three major blood cell lineages, the lymphoid, myeloid or erythroid cell lineages. The lymphoid lineage is comprised of B cells and T cells, which collectively function in antibody production and antigen detection, thereby functioning as a cellular and humoral immune system. The myeloid lineage, which is comprised of monocytes (macrophages), granulocytes (including neutrophils), and megakaryocytes, monitors the bloodstream for antigens, scavenges antigens from the bloodstream, fights off infectious agents, and produces platelets, which are involved in blood clotting. The erythroid lineage is comprised of red blood cells, which carry oxygen throughout the body.

The stem cell population constitutes only a small percentage of the total cell population in the bone marrow. The stem cells as well as committed progenitor cells destined to become neutrophils, erythrocytes, platelets, etc., may be distinguished from most other cells by the presence of the particular progenitor "marker" antigen that is present on the surface of these stem/progenitor cells. A group of antibodies that is capable of recognizing this particular marker antigen is referred to as "cluster of differentiation 34" or "CD34". The designation "CD34+" is used to describe a cell as one that has the particular cell surface antigen that is recognized by the CD34 group of antibodies. Stem cells, then, are CD34+. The majority of cells that are CD34+ in bone marrow, however, are B lymphocyte progenitor cells and myeloid progenitor cells.

Neutrophils differentiate from stem cells through a series of intermediate precursor cells, which can be distinguished by their microscopic morphological appearance, including such characteristics as the size of their nuclei, the shape of their nuclei, cell size, nuclear/cytoplasmic ration, presence/absence of granules, and staining characteristics (see FIG. 1 and *Atlas of Blood Cells: Function and Pathology*, second edition, Zucker-Franklin et al.). Initially, the multipotent stem cell, which cannot be measured directly in vitro, gives rise to myeloid "progenitor cells" that generate precursors for all myeloid cell lines. The first myeloid progenitor is designated CFU-GEMM for "colony forming unit—granulocyte, erythroid, macrophage and megakaryocyte". In all of these descriptive terms, "colony" refers to a cell that is capable of giving rise to more than 50 cells as measured in 14 day in vitro assays for colony growth, under conditions as set forth in Example 5 of the present specification. These cells will divide at least six times.

The CFU-GM is committed progenitor—in other words, it is committed to differentiating into granulocytes and macrophages only. It is neither capable of differentiating into other types of cells nor is it capable of dedifferentiating into earlier stage progenitor cells. The CFU-GM progenitor cell may then differentiate into a myeloblast. The time required for differentiation from a CFU-GEMM to a myeloblast is believed to be about 1–4 days. A myeloblast is the first of the series of cells that may be referred to as "precursors" to the neutrophils, as such cells, once allowed to fully develop (differentiate), can only form neutrophils, which are only capable of undergoing fewer than six cell divisions and, therefore, do not form colonies in in vitro colony assays as described previously.

Once differentiation has progressed to the myeloblast stage, the myeloblasts undergo terminal differentiation into promyelocytes, which, in turn, differentiate into myelocyte over a course of about 4–6 days. Within another 5 days or so, myelocyte differentiate into metamyelocytes, which in turn, differentiate into banded neutrophils. These banded neutrophils finally differentiate into mature, segmented neutrophils, which have a half-life of about 0.3 to 2 days. The term "progenitor" will be used to refer to stem cells, and cells which can form colonies. "Precursor" will be used to refer to myeloblasts, promyelocytes and myelocyte an, in some instances, metamyelocytes and banded neutrophils, also.

During this progressive, morphologic differentiation, changes in the surface antigens of these cells can be observed. For example, stem cells, CFU-GEMM and CFU-GM are CD34+. Hematopoietic cells that differentiate beyond the CFU-GM state are no longer CD34+. Similar progressions of expression are observed for the cell-surface antigens CD33 and CD45RA. All neutrophil precursor cells subsequent to the promyelocyte precursor cells may be characterized as CD34–, CD33+, CD38+, CD13+, CD45RA–, and CD15+. More mature cells also may be characterized as CD11b+ and CD16+. (Terstappen et al. Leukemia 4:657, 1990). It should be appreciated, however, that such transitions in cell-surface antigen expression are gradual, rather than abrupt, wherein some cells of a particular precursor cell type may be positive and other cells of the same type may be negative for a particular cell-surface antigen. Furthermore, the determination that a particular cell type is positive or negative for a particular cell-surface antigen will depend, in part, upon the particular method used to make that determination. The characterization of cell differentiation by cell-surface antigen expression may be confirmed by other means of characterizing cell differentiation, such as cell morphology.

Specific growth factors react with specific receptors on stem cells to direct their differentiation into committed progenitor cells. These actors regulate the proliferation and differentiation of hematopoietic cells. At least four colony-stimulating factors (CSFs) are known to cooperate in the regulation of neutrophil production. These four factors, which are referred to as GM-SCF (granulocyte and macrophage), IL-3 (interleukin-3), G-CSF (granulocyte), and M-CSF (macrophage), which is also known as CSF-1, are synthesized by macrophages, T cells, endothelial cells and other types of cells, The potential of a progenitor cell to respond to a CSF is determined in part, by the presence of receptors on the surface of the cell for that particular CSF and, in part by the concentration of the particular CSF. There also is some indication for indirect stimulation, whether via an accessory cell or by synergistic action with other obligatory growth factors, such as c-kit ligand, IL-6 (interleukin-6), IL-11 (interleukin-11), IL-4 (interleukin-4), and IL-1 (interleukin-1).

In addition to changes in morphology and cell-surface antigen expression, as neutrophil precursor cells differentiate, they lose their capacity to proliferate. In general, the less mature neutrophil precursor cells, namely the myeloblasts, promyelocytes, and myelocyte, retain their ability to proliferate. However, the more mature neutrophils, namely the metamyelocytes and the banded neutrophils, lose their capacity to proliferate, although they continue to differentiate into mature, segmented neutrophils.

Several methods of treatment have been proposed to combat HDC-induced neutropenia. These methods can partially ameliorate the neutropenia but cannot eliminate it completely. Bone marrow cells alone have been used to provide the cellular component necessary for neutrophil recovery. However, this particular method of treatment only reduces the period of neutropenia to about 2–3 weeks.

Several problems are associated with the use of bone marrow to reconstitute a compromised hematopoietic system. First, the number of stem cells in bone marrow is very limited. Stem and progenitor cells make up a very small percentage of the enucleated cells in the bone marrow, spleen, and blood. About ten times fewer of these cells are present in the spleen relative to the bone marrow, with even less present in the adult blood. As an example, approximately one in one thousand nucleated bone marrow cells is a progenitor cell; stem cells occur at a lower frequency. Secondly, a significant period of time is necessary for a stem cell to differentiate to a mature neutrophil, on the order of at least 10–15 days.

Bone marrow gathered from a different (allogeneic) matched donor has been used to provide the bone marrow for transplant. Unfortunately, Graft Versus Host Disease (GVHD) and graft rejection limits bone marrow transplantation even in recipients with HLA-matched sibling donors. Approximately half of the allogeneic bone marrow transplantation recipients develop GVHD. Current therapy for GVHD is imperfect and the disease can be disfiguring and/or lethal. Thus, risk of GVHD restricts the use of bone marrow transplantation to patients with otherwise fatal disease, such as malignancies, severe aplastic anemia, thalassemia, and congenital immunodeficiency states. About 7,000 of the 15,000 bone marrow transplantations performed each year are allogeneic. Many other patients have diseases that might be treated by marrow cell transplantation (such as sickle cell anemia) if GVHD or graft rejection were not such serious risks.

An alternative to allogeneic bone marrow transplants is autologous bone marrow transplants. In autologous bone marrow transplants, some of the patient's own bone marrow is harvested prior to treatment, such as HDC, and is transplanted back into the patient afterwards. Such a method eliminates the risk of GVHD. However, autologous bone marrow transplants still present many of the same problems presented by allogeneic bone marrow transplants in terms of the limited number of stem cells presenting the bone marrow and the amount of time required for a stem cell to differentiate to a mature neutrophil. In addition, autologous marrow also may be contaminated with tumor cells.

One approach to overcome the problems with bone marrow transplants has been the attempted isolation of stem cells form donated bone marrow, or other sources, and the use of such stem cells to regenerate the immune system, such as after HDC. The theory behind this approach in the allogeneic setting is that the stem cell is naive in nature (has not developed significant host-specific characteristics) and, therefore, will not be recognized in the transplant recipient as a foreign body or antigen, thus hopefully improving acceptance. Furthermore, since these isolated cells contain minimal numbers of T-cells, it may be possible to avoid adverse reactions, as in GVHD.

Problems are also associated with this approach. Since the number of stem cells in bone marrow is very limited and at least about 10–15 days is required for stem cells to differentiate into mature neutrophils, significant in vitro multiplication of the cells must take place in order to generate an adequate number of neutrophils for introduction into the patient. Thus, the transplantation of stem cells at best results in an immunocompromised patient continuing to be immunocompromised for a significant period of time.

Hematopoietic growth factors, such as G-CSF or GM-CSF, have been administered alone or combination with autologous or allogenic transplants of stem cell populations subsequent to HDC. Although neutrophils increase in number as a result of the treatment, the period of severe neutropenia is only reduced to about ten days. Since the production of neutrophils form stem cells normally takes about 10–15 days, stimulation of progenitor cell production and differentiation by hematopoietic growth factors and the eventual reconstitution of mature leukocytes, including mature neutrophils, requires a significant period of time.

Peripheral blood stem cells (PBSC), which have been mobilized with chemotherapy or growth factors, also have been used to create neutropenia. It is believed that the mobilized PBSC represent a mixture of progenitor cells and, perhaps, precursor cells that occur naturally during the recovery of myelosuppressed bone marrow. Again, such a mixture of progenitor and, perhaps, precursor cells only reduces neutropenia to about nine days. Furthermore, the precursor cells in these mixtures probably would not survive freezing, since cells containing granules do not freeze well using presently known methods, and, therefore, could not be stored for subsequent treatments.

Generally speaking, none of these methods is successful in reducing the period of severe neutropenia below about 8–10 days. Such a lengthy period of neutropenia still renders the patient susceptible to infections, the treatment of which requires hospitalization at a significant cost.

Transfusions of mature neutrophils also have been attempted as a means of addressing neutropenia. Such transfusions can be very expensive and involve healthy donors in a procedure that is time consuming, uncomfortable, and risky (Clift et al, Symposium on Infectious Complications of Neoplastic Disease (Part II), Vol. 76:631–636 (1984)). A major concern in the use of mature neutrophil transfusion is that, if transfused mature neutrophils are unable to function and circulate normally in the recipient individual, toxic reactions may result with adverse consequences (Wright, The American Journal of Medicine, Vol. 76 637:644 (1984)).

U.S. Pat. No. 4,714,680 describes a suspension of human lympho-hematopoietic stem cells substantially free of mature lymphoid and myeloid cells but which may further comprise colony forming cells. Such a composition could be used in the treatment of neutropenia, however, given the fact that the production of neutrophils from stem cells requires about 10–15 days, such a composition would not reduce the period of neutropenia.

U.S. Pat. No. 5,004,681 relates to hematopoietic stem and progenitor cells of neonatal or fetal blood that are cryopreserved, and the therapeutic uses of such stem and progenitor cells upon thawing. In particular, the invention relates to the therapeutic use of fetal or neonatal stem cells for hematopoietic (or immune) reconstitution.

U.S. Pat. No. 5,061,620 describes a method to obtain a cellular composition of human hematopoietic stem cells, with fewer than 5% of lineage-committed cells. Such a composition also could be used in the treatment of neutropenia but, once again, such a composition would not reduce the period of neutropenia, since 10–15 days would be required for neutrophils to differentiate from stem cells and CFU-GEMM.

U.S. Pat. No. 5,087,570 relates to concentrated hematopoietic stem cell compositions that are substantially free of differentiated or committed hematopoietic cells. The cells are obtained by substraction of cells having certain particular markers and selection of cells having other particular markers. The resulting compositions may be used to provide for individual or groups of hematopoietic lineages to reconstitute stem cells of the host, and to identify and assay for a variety of hematopoietic growth factors.

There remains a need for an effective means of treatment to significantly reduce, if not completely eliminate, the period of neutropenia. Such a treatment would enable a patient, who has undergone HDC or some other form of chemotherapy, such as that associated with conventional oncology therapy, to combat infection, thereby reducing, if not completely eliminating, the risks of morbidity and death. Similar benefits would be realized for patients suffering from drug, toxin, radiation or disease-induced neutropenia or genetic/congenital neutropenia. In addition, such a treatment also could be used to treat a patient who, although not suffering form severe neutropenia, has a reduced level of neutrophils.

SUMMARY OF THE INVENTION

The present invention provides a composition of human neutrophil precursor cells, wherein the cellular component is comprised of at least about 16% myeloblasts and promyeloblasts and less than about 5% colony forming units (CFU) that give rise to at least about 50 cells. Alternatively, the cellular component of the composition may be comprised of at least about 16% CD15+CD11b− cells, at least about 60% of which are myeloblasts and promyelocytes. The myeloblasts and promyelocytes have the capacity to proliferate and differentiate into segmented neutrophils. The neutrophil precursors may be purified so as to be substantially free of erythroid lineage-committed cells, including BFU-E. The compositions may additionally comprise myelocyte, metamyelocytes, banded neutrophils, and/or segmented neutrophils. The myelocyte, metamyelocytes, banded neutrophils, and/or segmented neutrophils may be derived from the neutrophil precursor cells in vitro. The neutrophil precursor cells, themselves, may be derived from peripheral blood, bone marrow, or cord blood.

The present invention also provides a method of treating a patient suffering form neutropenia, which may result from HDC, conventional oncology therapy, drugs, diseases, genetic disorders, toxins, and radiation, as well as a method of treating a patient who, although not suffering form severe neutropenia, has a reduced population of neutrophils. The method comprises the administration of a composition as described above. The method of administration may be intravenous and may be supplemented by the administration of stem cells and other lineage-uncommitted cells.

The present invention further provides a method of gene therapy, which comprises the stable introduction of a gene, such as a gene for resistance to a chemotherapeutic drug or an absent or aberrant neutrophil constituent, into neutrophil progenitor cells, the subsequent in vitro culture of the neutrophil progenitor cells to proliferate and differentiate into neutrophil precursor cells, and the administration of a composition comprising the genetically altered neutrophil precursor cells to a patient, who will be exposed to the chemotherapeutic drug, by intravenous injection, for example, or for correction of a neutrophil anomaly. Alternatively, the gene may be introduced into the neutrophil precursor cells for administration to the patient.

Also provided is a method for preparing a suspension of human neutrophil precursor cells. The method consists of: a) obtaining hematopoietic stem/progenitor cells, and b) culturing the stem/progenitor cells in the presence of at least one hematopoietic growth factor so as to obtain human neutrophil precursor cells wherein the cellular component consists of at least 16% myeloblasts and promyelocytes and less than about 5% colony forming units. Growth factors which can be used are, for example, G-CSF, GM-CSF, IL-3, IL-6, SCF or recombinant proteins containing one or more active moieties of these or other hematopoietic growth factors.

Further provided is a method of promoting the proliferaton of human neutrophil precursors. The method consists of: a) obtaining a suspension of human neutrophil precursors wherein the cellular component consists of at least about 16% myeloblasts and promyleocytes and less than about 5% colony forming units, and b) culturing said suspension in the presence of at least one hematopoietic growth factor. Growth factors which can be used are, for example, G-CSF, GM-CSF, IL-3, SCF or recombinant proteins containing one or more active moieties of these or other hematopoietic growth factors.

The invention also provides a method of treating a patient having a reduced population of neutrophils. The method consists of administering to the patient a composition of human neutrophil precursor cells wherein the cellular component consists of at least 16% myeloblasts and promyelocytes and less than about 5% colony forming units and at least one hematopoietic growth factor. Growth factors which can be used are, for example, G-CSF, GM-CSF, IL-3, SCF or recombinant proteins containing one or more active moieties of these or other hematopoietic growth factors.

Also provided are hematopoietic cell suspensions. The cell suspensions consist of human neutrophil precursor cells and at least one hematopoietic growth factor. The cellular component of such cell suspensions consists of at least about 16% myleoblasts and promyleocytes and less than about 5% colony forming units. Growth factors which can be used are, for example, G-CSF, GM-CSF, IL-3, SCF or recombinant proteins containing one or more active moieties of these or other hematopoietic growth factors.

Additional inventive features and advantages of the present invention will become apparent form the description that follows.

DETAILED DESCRIPTION OF THE PREFERRED EMBODIMENTS

Figure 1:
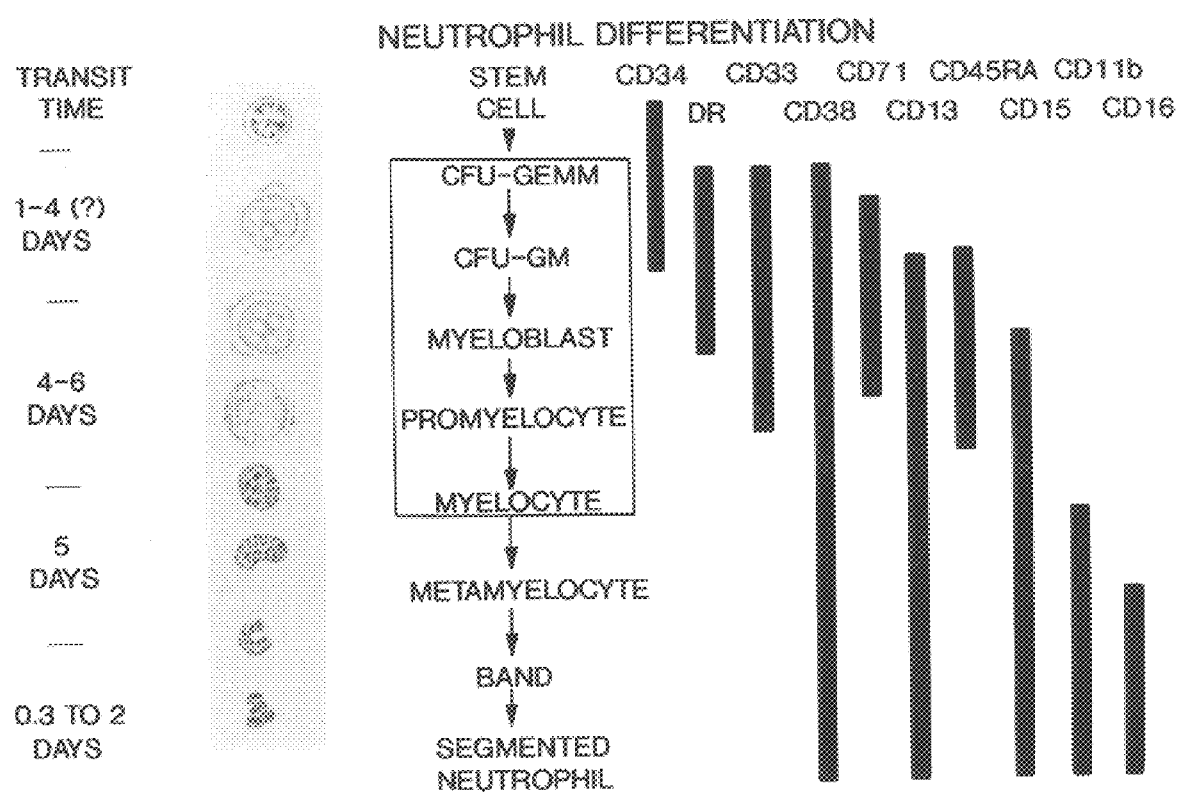
FIG. 1: Neutrophil differentiation in terms of cell morphology, cell-surface antigen expression, and transit time.

The present invention provides an enriched population of human neutrophil precursor cells. The enriched population of human neutrophil precursor cells is derived from the in vitro culture of human stem and/or neutrophil progenitor cells. The human stem and/or neutrophil progenitor cells may be obtained from bone marrow or peripheral blood stem cells (PBSC), although other hematopoietic cell sources, whether fetal, such as umbilical cord blood or liver, neonatal or adult, may be used. The particular source of human neutrophil progenitor cells will depend, in part, upon the particular use to which the resulting population of neutrophil precursor cells will be applied.

Although any source of human neutrophil progenitor cells may be used in research applications, bone marrow, in particular autologous bone marrow as opposed to allogenic bone marrow, and peripheral blood CD34+ cells are preferred sources of human neutrophil progenitor cells for the therapeutic treatment of a patient undergoing oncology support or of a patient experiencing neutropenia subsequent HDC. Such cell sources are also preferred for the therapeutic treatment of a patient suffering from neutropenia that has been induced by a disease, drug, toxin, or radiation or from genetic neutropenia. Furthermore, such cell sources are also useful to treat patients who do not have neutropenia per se but have reduced populations of neutrophils.

Bone marrow cells may be obtained from a source of bone marrow, such as the iliac crest, tibia, femur, sternum, or another bone cavity. Bone marrow may be aspirated form the bone in accordance with techniques that are well known to those who are skilled in the art. The marrow may be harvested from a donor, in the case of an allogeneic transplant, or from the patient, himself, in the case of autologous transplant. The marrow may be processed as desired, depending mainly upon the use intended for the recovered cells.

White blood cells, in particular mononuclear cells (MNC), may be collected from the peripheral blood by leukapheresis. The MNC are then passed through a device containing a monoclonal antibody, such as CD34 or other stem/progenitor recognition systems, linked to a solid phase. The CD34 monoclonal antibody binds CD34+ cells, which include neutrophil progenitor cells, and the remainder of the cells pass through the device without being bound. Once a sufficient number of neutrophil progenitor cells has been isolated, the patient is disconnected from the device. The advantage of such a method is that it allows extremely rare peripheral blood stem cells to be harvested from a very large volume of blood, sparing the donor the expense and pain of harvesting bone marrow and the associated risks of anesthesia, analgesia, blood transfusion, and infection.

The neutrophil progenitor cells obtained from other sources may be initially separated from other cells by a relatively crude separation. Large numbers of lineage-committed cells, such as those cells committed to differentiate along erythroid and lymphoid cell lineages, may be removed, if desired. However, it will be appreciated by one who is skilled in the art that it is not necessary to remove any or every undesired class of lineage-committed cells from the neutrophil progenitor cells. Since some from of positive selection may be employed in any purification protocol, the undesired lineage-committed cells would not be selected. It is preferred that there be some from of negative selection for all of the undesired lineage-committed cells initially so that the number of such cells in a final positive selection of neutrophil progenitor cells is minimize. By using combination of negative selection, i.e., cell removal, with positive selection, i.e., cell isolation, a substantially homogeneous population of neutrophil progenitor cells may be obtained.

Various techniques may be used to separate the neutrophil progenitor cells from other lineage-committed cells. For relatively crude separations, i.e., separations where up to 10%, usually not more than about 5%, generally not more than about 1%, of the total cells present have the positively selected marker, e.g., CD34, various techniques of differing efficacy may be employed. The separation viability of the fraction of the cells to be collected. The particular technique employed will, of course, depend upon the efficiency of separation, cytotoxicity of the method, the ease and speed of separation, and what equipment and/or technical skill is required.

Separation procedures may include magnetic separation, using antibody-coated magnetic beads, affinity chromatography, cytotoxic agents, either joined to a monoclonal antibody or used in conjunction with complement, and "panning", which utilizes a monoclonal antibody attached to a solid matrix, or another convenient technique. Antibodies attached to magnetic beads and other solid matrices, such as agarose beads, polystyrene beads, hollow fiber membranes and plastic petri dishes, allow for direct separation. Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well within the skill in the art.

The unbound cells then can be eluted or washed away with physiologic buffer after sufficient time has been allowed for the CD34+ cells to bind to the solid-phase linked antibodies. The bound cells are then separated from the solid phase by any appropriate method, depending mainly upon the nature of the solid phase and the antibody employed.

Antibodies may be conjugated to biotin, which then can be removed with avidin or streptavidin bound to a support, or fluorochromes, which can be used with a fluorescence activated cell sorter (FACS), to enable cell separation. A FACS employs a plurality of color channels, low angle and obtuse light-scattering detection channels, and impedance channels, among other more sophisticated levels of detection, to separate or sort cells. Any technique may be employed as long as it is not detrimental to the viability of the desired cells.

The progenitor cells initially may be separated from other cells by the cell-surface expression of CD34. For example, CD34+ cells may be positively selected by magnetic bead separation, wherein magnetic beads are coated with CD34-reactive monoclonal antibody. The CD34+ cells then may be removed from the magnetic beads. Release of the CD34+ cells from the magnetic beads may be effected by culture release or other methods. Purity of the isolated CD34+ cells may be checked with a FACSCAN® flow cytometer (Becton Dickinson, San Jose, Calif.), for example, if so desired. Enrichment of CD34+ cells is preferred to minimize the volume of culture medium used and to remove accessory cells, both alive and dead or dying, which may produce factors that affect the subsequent proliferation and differentiation of the selected cells in culture. However, the enriched CD34+ population of cell does not necessarily have to be pure.

The resulting enriched population of neutrophil progenitor cells then may be cultured to proliferate and differentiate into neutrophil precursor cells. Enriched preparations of CD34+ cells may be placed in a suitable medium in culture plates. Conveniently, the medium in culture plates is one that is well-defined and enriched. An example of a suitable medium is McCoy's 5A culture medium (Sigma, St. Louis, Mo.), which additionally contains fetal bone serum (Hyclone, Logan, Utah), horse serum (Hyclone), hydrocortisone (Sigma), α-thioglycerol, and gentamicin (Gibco). The culture medium should further comprise hematopoietic growth factors, such as recombinant IL-3 (rIL-3), recombinant G-CSF (rG-CSF), recombinant GM-CSF (rGM-CSF) (Amgen, Thousand Oaks, Calif.), C-kit ligand (steel factor), and stem cell factor (Genzyme, Boston, Mass.). It will be appreciated by one who is skilled in the art that other suitable culture media may be used as well as other suitable hematopoietic growth factors in various combinations. For example, the combination of IL-3, G-CSF and GM-CSF as described in Example 2 or, alternatively, various combinations such as IL-3/GM-CSF, IL-3/SCF/IL-6, IL-3/SCF/IL-6/G-CSF and IL-3/G-SCF/GM-SCF/SCF can be used as well to differentiate the cells into neutrophil precursors. Also, recombinant fusion proteins containing one or more active moieties of a hematopoietic growth factor can be used as well. A specific example of such a fusion protein is one containing the active moieties for IL-3 and GM-CSF.

It is preferred that the culture medium not be replaced during the period of culturing, although the cultures should be fed at weekly intervals. However, in some cases, it may be desirable to change the culture medium from time to time, at least about once or twice per week.

CD34+ enriched cell populations obtained from bone marrow, however, may contain significant numbers of CD19+CD34+ cells that do not proliferate under certain culture conditions, such as those described above. It will be appreciated by one who is skilled in the art that a greater proliferation of neutrophil precursor cells possibly could be obtained using bone marrow CD34+ cells that have significantly, if not completely, depleted of CD19+ cells or, alternatively, CD34+ cells could be obtained from cord or peripheral blood, where the population of CD19+ cells is greatly reduced.

At selected days during the culture period, cell aliquots may be removed and labeled with fluorescent-conjugated CD15 and CD11b monoclonal antibodies for sorting in a flow cytometer, such as the FACSCAN® flow cytometer (Becton Dickinson, San Jose, Calif.), based on expression of CD15 and CD11b cell-surface antigens. Cells sorted according to CD15 and Cd11b antigen expression may be additionally characterized according to morphology and potential for colony-forming units. Cells may be characterized by morphology as myeloblasts, promyelocytes, myelocytes, metamyelocytes, banded neutrophils, segmented neutrophils, promonocytes and monocytes. Colony assays may be conducted in methyl cellulose containing other media components and growth factors to determine the existence of CFU-GM, CFU-M, BFU-E, and CFU-GEMM.

After culturing for an appropriate length of time, CD15+ Cd11b– cells, which are at least about 60% myeloblasts and promyelocytes, may be isolated and utilized in the therapeutic treatment of patients suffering from neutropenia. The length of time in culture necessary to obtain neutrophil precursor populations will depend on the inherent variation within the patient from which the sample was obtained. The neutrophil precursor cells may be administered in the from of a composition, wherein the cellular component is comprised of at least about 16% myeloblasts and promyelocytes and less than about 5% colony forming units (CFU) of at least about 50 cells. Alternatively, the cellular component of the composition cellular component is comprised of at least about 16% myeloblasts and promyelocytes and less than about 5% colony forming units (CFU) of at least about 50 cells. Alternatively, the cellular component of the composition may be comprised of at least about 16% CD15+CD11b− cells, at least 60% of which are myeloblasts and promyelocytes, and less than about 5% colony forming units (CFU) of at least about 50 cells. The myeloblasts and promyelocyctes have the capacity to proliferate and differentiate into segmented neutrophils. The compositions may be purified to be substantially free of erythroid lineage-committed cells, including BFU-E. The compositions may additionally comprise myelocytes, metamyelocytes, banded neutrophils, and/or segmented neutrophils. The myelocytes, metamyelocytes, banded neutrophils, and/or segmented neutrophils may be derived from the neutrophil precursor cells in vitro.

The cellular component of the present inventive compositions is enriched for neutrophil precursor cells, in particular myeloblasts and promyelocytes, over that which is found normally in bone marrow. For example, in adults, the upper limit of the combined ranges of myeloblasts and promyeloblasts in number fraction as percent is 12.5%. It is also 12.5% in newborns approaching infancy and preschool children. It is 15.0% in infants and school-age children and only 10.0% in day-old newborns. (Geigy Scientific Tables, Vol 3, C. Lentner, ed. Ciba-Geigy, Basel, Switzerland. 1984).

The neutrophil precursors can, for example, be stored for later usage as described below or they can be further expanded to obtain a larger population of precursor cells. Such further proliferation in culture is advantageous when it is necessary to use a relatively large number of neutrophil precursors for a particular application or if it is desired to produce multiple samples of neutrophil precursors from a single isolate. Further expansion or proliferation of the neutrophil precursor cells is accomplished by, for example, subsequent culture of the cells in at least one hematopoietic growth factor. More than one hematopoietic growth factor and various combinations of such growth factors can be used to enhance the continued proliferation of the neutrophil precursor cells. The growth factors or combinations thereof can be the same or different from those used to obtain the initial population of neutrophil precursors. For example, proliferation of neutrophil precursors can be enhanced by adding or substituting the growth factors present in the cultures with hematopoietic growth factor combinations such as G-CSF and GM-CSF or IL-3 and SCF. Individual growth factors will also promote the proliferation of neutrophil precursors in culture. For example, any one of G-CSF, GM-CSF, IL-3 and SCF can be used alone to promote proliferation. Other hematopoietic growth factors known to one skilled in the art can be used as well to promote or enhance the proliferation of neutrophil precursor cells. Using the teachings described herein and the methods set forth in the Examples, one skilled in the art can determine which other growth factors can be used to culture neutrophil precursors.

The composition may be administered intravenously to a patient requiring a bone marrow transplant in an amount sufficient to reconstitute the patient's hematopoietic and immune systems. The composition may be supplemented with stem cells and other linage-uncommitted cells. Precise, effective quantities can be readily determined by those who are skilled in the art and will depend, of course, upon the exact condition being treated by the particular therapy being employed.

Neutrophil compositions can be administered alone, as described above, or in combination with hematopoietic growth factors that promote their proliferation, differentiation or viability. Co-administration of growth factors to augment therapeutic treatment of neutropenia is advantageous because it allows for a larger number of mature neutrophils to be produced in a shorter period of time then what can be obtained by administration of neutrophil precursors alone. The growth factors can be administered directly with the cell suspension or indirectly by separate injection into the patient. One skilled in the art will know or can determine whether direct or indirect administration of growth factors is appropriate for a particular therapeutic treatment. Further, growth factors can, for example, be administered individually or in combinations to augment the therapeutic treatment. The above described growth factors and combinations thereof which promote the proliferation of neutrophil precursors are specific examples of such factors which can be administered in combination with neutrophil precursors.

A survey of published reports indicates that the number of CFU-GM infused for autologous bone marrow reconstitution in human patients can be relied on as an indicator of the potential for successful hematopoietic reconstitution (Spitzer, G., et al., 1980, Blood 55(2):317–323; Douay et al, 1986, Exp. Hematol. 14:358–365). By standardizing published data by patient weight, and assuming a patent weight of 150 pounds (67.5 kilograms), the calculated number of CFU-GM needed for successful hematopoietic reconstitution using autologous bone marrow cells ranges from $2$–$425 \times 10^4$/kg patient weight, with faster recovery noted using greater than $10 \times 10^4$ CFU-GM. Accordingly, it is anticipated that the administration of compositions of the present invention comprising an equivalent or greater number of neutrophil and/or neutrophil precursor cells, either alone or in combination with stem/progenitor cells, should result in the successful reconstitution of a human hematopoietic system in even shorter time.

Because of the unique aspect of the present invention, in which the neutrophil precursor cells have the capacity to both proliferate and differentiate in culture and remain viable for an extended period of time, it is possible to isolate and initial quantity of cells from the in vitro culture and to administer that quantity of cells to the patient. After a period of time, one or more additional aliquots of viable neutrophil and or neutrophil precursor cells may be isolated from culture and administered to the patient.

The neutrophil precursor cells may also find use in the treatment of neutropenia induced by a disease, drug, toxin or radiation, as well as genetic or congenital neutropenia. For example, aberrant neutrophil precursor cells may be treated by genetically modified autologous or allogeneic neutrophil precursor cells. Such gene therapy may involve the introduction of a wild-type gene into the neutrophil precursor cell or its progenitor cell, either by homologous or random recombination, for example. Similarly, drug resistance genes may be introduced into neutrophil precursor cells or their progenitor cells to enable neutrophil precursor cells and subsequently differentiated, more mature neutrophil cells to be resistant to one or more drugs, in particular, the drugs used in chemotherapy. Such neutrophil cells could be transplanted into a patient, either before or while undergoing chemotherapy, thereby eliminating the risk of neutropenia induced by chemotherapeutic agents. Diseases other than those specifically related to neutrophils may be treated, where the disease is related to the lack of a particular secreted product, such as a hormone enzyme, interferon, factor, etc. Production of the protein that parallels natural production may be attained, even though production of the protein will be in a different cell type from that which normally produces such a protein, by employing the appropriate regulatory sequences for inducible gene expression. Alternatively, a ribozyme, antisense or other message may be inserted into the neutrophils to inhibit particular gene products or susceptibility to disease.

The neutrophil precursor cells also may be used to treat human patients who are not severely neutropenic but who have reduced levels of neutrophils. Such populations of cells could be used to supplement existing reduced populations of neutrophils in the patient to the cell population numbers. In general, a normal healthy range of neutrophils is considered to be from about 1,800 neutrophils/µl blood to about 7,000 neutrophils/µl blood. Some patients may have levels of neutrophils as low as about 500 neutrophils/µl blood, yet clinically do not appear to be ill. However, patients with neutrophil levels below about 500 neutrophils/µl blood are considered to be neutropenic and at risk for infections and fever.

The neutrophil precursor cells also may be used in the research of the proliferation and differentiation of neutrophils. For example, factors associated with proliferation and differentiation, such as hematopoietic growth factors, may be evaluated. In additions, cytokine combinations and extracellular conditions may be evaluated. Similarly, the cells, themselves, may be used to evaluate particular media and fluids for cell proliferative and/or differentiative activity; etc.

The neutrophil precursor cells possibly may be frozen in liquid nitrogen for long periods of storage. The cells then may be thawed and used as needed.

Cryoprotective agents, which can be used, include but are not limited to dimethyl sulfoxide (DMSO) (Lovelock, J. E. and Bishop, M. W. H., 1959, Nature 183:1394–1395; Ashwood-Smith, M. J., 1961, *Nature* 190:1204–1205), hetastarch, glycerol, polyvinylpyrrolidone (Rinfret, A. P., 1960, *Ann, N.Y. Acad. Sci.* 85:576), polyethylene glycol (Sloviter, H. A. and Ravdin, R. G., 1962, *Nature* 196:548), albumin, dextran, sucrose, ethylene glycol, i-erythritol, D-ribitol, D-mannitol (Rowe, A. W., et al., 1962, *Fed. Proc.* 21:157), D-dorbitol, i-inositol, D-lactose, Choline chloride (Bender, M. A., et al, 1960, *J. Appl. Physiol.* 15:520), amino acids (Phan the Tran and Bender, M. A., 1960, *Exp. Cell Res.* 20:651), methanol, acetamide, glycerol monoacetate (Lovelock, J. E., 1954, *Biochem, J.* 56:265), and inorganic salts (Phan The Tran and Bender, M. A., 1960, *Proc. Soc. Exp. Biol. Med.* 104:388; Phan The Tran and Bender, M. A., 1961, *Radiobiology, Proceedings of the Third Australian Conference on Radiobiology*, Ilbery, P. L. T., ed., Butterworth, London, p. 59).

Typically, the cells may be stored in 10% DMSO, 50% serum and 40% RPMI 1640 medium. Once thawed, the cells may be induced to proliferate and further differentiate by the introduction of the appropriate hematopoietic growth factors.

Alternatively, the neutrophil precursor cells could be allowed to immediately proliferate and differentiate into mature neutrophil cells in culture, by providing the appropriate growth factors. Mature neutrophils cultured in accordance with the present invention are capable of being cultured for about 4–5 weeks. This is significantly longer than the typical survival of freshly isolated neutrophils, which is only 72 hours or less, even when cultured in the presence of growth factors.

The following examples serve to further illustrate the present invention but are not intended to limit the scope of the invention.

EXAMPLE 1

This example describes a preferred method of enriching a population of CD34+ cells by positive selection.

Mononuclear cells were isolated from bone marrow on 1.077 g/dl Histopaque (Sigma, St. Louis, Mo.). The cells were washed in calcium/magnesium-free phosphate-buffered saline (CMF-PBS, Gibco, Grand Island, N.Y.) and were resuspended in Iscoves-modified Dulbecco's Medium (IMDM, Sigma) containing 2% fetal bovine serum (Hyclone, Logan, Utah) to a concentration of $1 \times 10^7$ cells/ml. The cells were then contacted with magnetic beads, which were coated with sheep anti-mouse IgG antibodies (Dynal, Oslo, Norway), sensitized with 1 µg of the anti-CD34 monoclonal antibody QBEND 10 (Quantum Biosystems, England) and used to capture CD34+ cells from the cell suspension. Essentially, CD34+ cells were positively selected as described by Strauss et al., AM. J. Ped. Hematol. Oncol. 13:217 (1991), with slight modification. The magnetic beads and cells were rotated for 30 minutes at 4° C. at 2.5 rpm at a bead:cell ratio of 1:1 or 5:1.

Following CD34 selection, the bead-cell complexes were isolated using a magnetic tube holder (Fenwal Div., Irvine, Calif.). After a series of washes in CMF-PBS, the CD34+ cells were released from the beads by adding 50 U/ml of Chymodiactin® (Bootes Pharmaceutical Co., Lincolnshire, Il.) in RPMI 1640 (Sigma) and incubating for 15 minutes in a water bath at 37° C.

The cells that were released from the beads were evaluated for CD34 purity by staining with the monoclonal antibody to CD34, namely FITC-8G12 (Fenwal), for 15 minutes on ice and quantitating the stained cells with a FACSCAN® flow cytometer (Becton Dickinson, San Jose, Calif.) using a side scatter vs. fluorescence display. The CD34+ cell population was resolved as a population having FITC fluorescence and low side scatter.

The level of purity of CD34+ cells obtained in accordance with this procedure averaged 66±16% (mean±1. S.D., n=7) with a range from about 40% to about 93% CD34+ as shown in Table I.

TABLE I

PRODUCTION OF NEUTROPHIL PRECURSORS AND
MATURE NEUTROPHILS IN CULTURES OF CD34+ CELLS

| Experiment # | Initial Cell Preparation | | Day of Culture | Fold Increase in Cell # | % CD15+ CD11b− Region B | % CD15+ CD11b+ Region C |
|---|---|---|---|---|---|---|
| | % CD34+ | % CD19+ of CD34+ | | | | |
| 1 | 54 | N.D. | 12 | 8.3 | 2 | 79 |
| 2 | 69 | N.D. | 12 | 6.9 | 50 | 47 |
| 3 | 93 | N.D. | 12 | 3.3 | 11 | 74 |
| 4 | 55 | 49 | 11 | 2.7 | 52 | 30 |
| 5 | 79 | 58 | 12 | 12.2 | 41 | 39 |
| | | | 26 | 48 | 8 | 91 |
| 6 | 40 | 55 | 12 | 7.8 | 45 | 36 |
| | | | 26 | 46 | 8 | 84 |

TABLE I-continued

PRODUCTION OF NEUTROPHIL PRECURSORS AND
MATURE NEUTROPHILS IN CULTURES OF CD34+ CELLS

| Ex-per-iment # | % CD34+ | Initial Cell Preparation % CD19+ of CD34+ | Day of Culture | Fold Increase in Cell # | % CD15+ CD11b- Region B | % CD15+ CD11b+ Region C |
|---|---|---|---|---|---|---|
| 7 | 72 | 73 | 10 | 3.7 | 58 | 12 |
|   |    |    | 35 | 74  | 17 | 83 |
| Mean | 66 | 59 | Mean (D10–12) | 6.4 | 37 | 45.3 |
| S.D. | 16 | 9 | | | | |

N.D. = Not Determined

EXAMPLE 2

This example describes a preferred method of culturing CD34+ cells in vitro.

The enriched preparations of CD34+ cells were placed into 4-well cell culture plates (Nunc, Thousand Oaks, Calif.) or 25–75 cm² flasks (Costar, Cambridge, Mass.) at an initial cell concentration of 1–2×10⁵ cells/ml in McCoy's 5A culture medium (Sigma) containing 12.5% fetal bovine serum (Hyclone), 12.5% horse serum (Hyclone). 10 μM α-thioglycerol (Sigma) and 10 μg/ml gentamicin (Gibco). The recombinant growth factors rIL-3, rG-CSF, and rGM-CSF (Amgen, Thousand Oaks, Calif.) were added at concentrations of 300 U/ml. 200 U/ml, and 300 U/ml, respectively.

The cultures were placed in a 5% $CO_2$/5% $O_2$, 37° C., high humidity incubator an incubated up to 37 days under these conditions. The cultures were fed at weekly intervals with the above-described culture medium, without medium replacement, to return the cell concentration to 1–2×10⁵ cells/ml.

Figure 2:
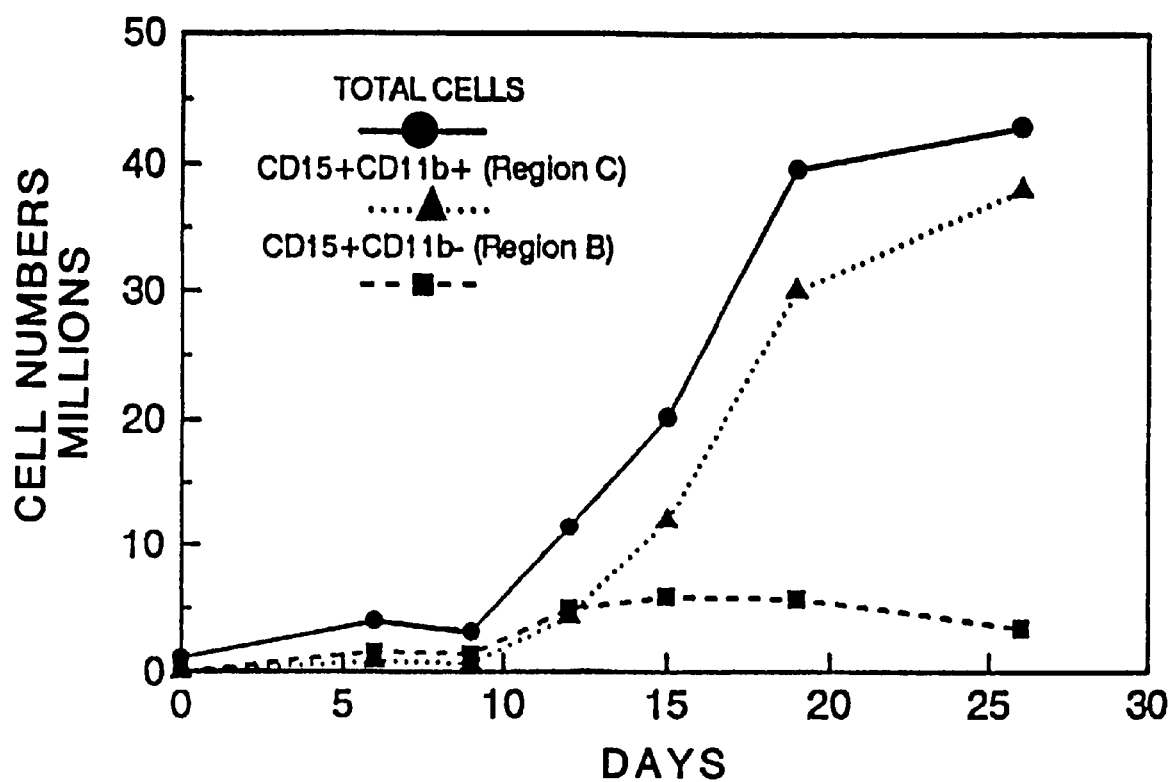
FIG. 2: Kinetics of a 26-day culture in which the total number of cells increased over 40 fold.
Figures 1, 5C:
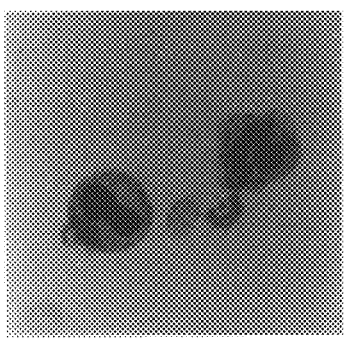
Figures 2, 5C:
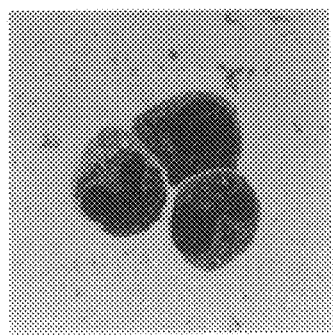
Figures 3, 5C:
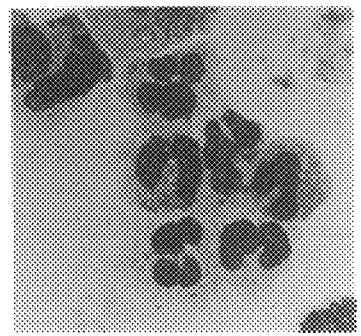
FIGS. 3A–3H: CD15 and CD11b differentiation during a 21-day culture of CD34+ cells.
FIGS. 5A, B, $C_1$, $C_2$, $C_3$, and D: Morphology of CD15 and CD11b sorted cells as shown in FIG. 4.
Figure 5A:
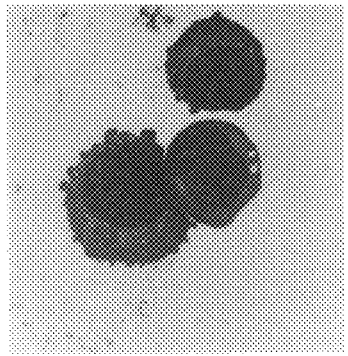
Figure 5B:
Figure 5D:
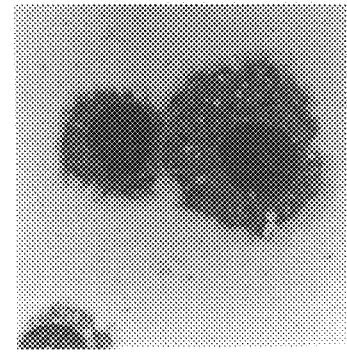

FIG. 2 shows that the CD34+ enriched cell population was capable of extensive proliferation in vitro. Total cell numbers increased gradually until day 10–12 at which time large increases were observed. Cell proliferation continued beyond 20 days in culture and cells generated in these cultures were capable of being viably maintained for up to about 37 days. The enriched CD34+ progenitor cells were capable of proliferating an average of 6.4±3.54 fold in 10–12 days and 56±15.6 fold after 26–35 days (see Table I). The proportion of CD34+ cells gradually declined such that, after 7–10 days of culture, less than about 5% of the cells were CD34+, indicating that the CD34+ neutrophil progenitor cells had differentiated into neutrophil precursor cells and mature, segmented neutrophils. The increase in mature, segmented neutrophils, wvidenced by the increase in CD15+ Cd11b+ cells, is shown in FIG. 3.

EXAMPLE 3

This example describes a method used to assess the changes in phenotypes of the cultured CD34+ cells.

On selected days during the culture of the CD34+ cells, aliquots of 1–2×10⁵ cells were removed from the culture late or flask and were washed once or twice in phosphate-buffered saline containing 0.05% bovine serum albumin and 0.1% azide (PAB). The cells were then labeled with CD15 (LeuM1) FITC-conjugated and CD11b (Leu15) PE-conjugated monoclonal antibodies (Becton Dickinson) for 10 minutes on ice. After one additional wash in PAB, the cells were suspended in 1 ml of PAB and analyzed using the FACSCAn® flow cytometer (Becton Dickinson) for expression of CD15 and CD11b.

Figure 4C:
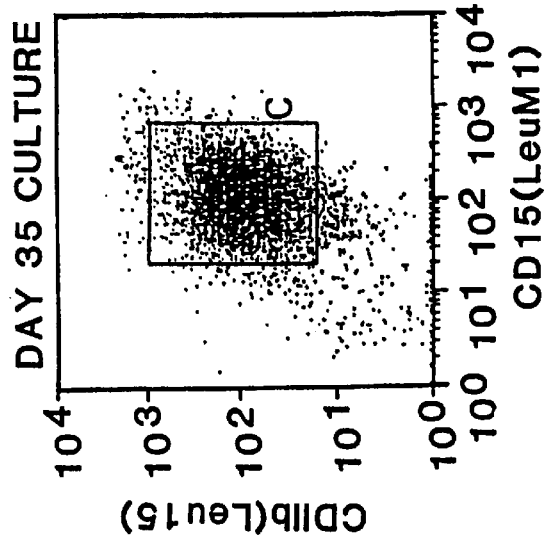
FIGS. 4A–4C: CD15 and CD11b sorted cells for determination of morphology as shown in FIG. 5.
Figure 4B:
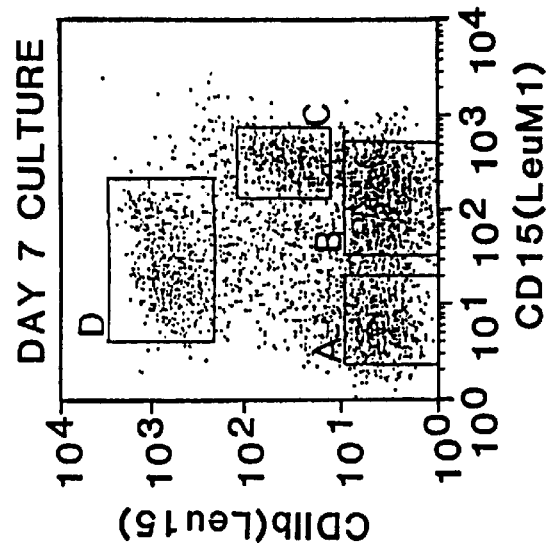
Figure 4A:
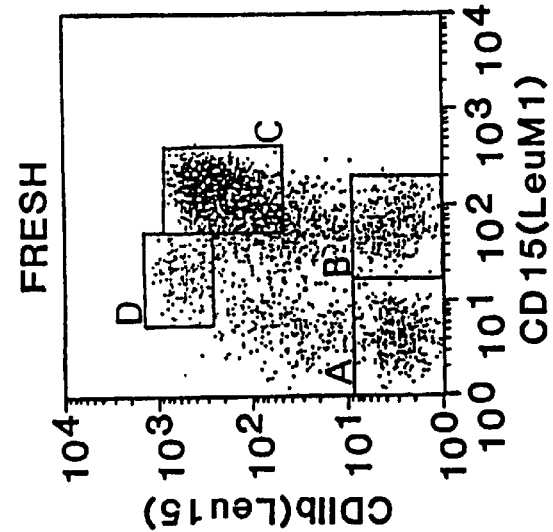

Pre-enrichment bone marrow cells (day 0) contain a large population of CD15+Cd11b+ cells, as shown in FIG. 3 and region C of FIG. 4. This population of CD15+CD11b+ cells represents metamyelocytes, banded neutrophils and segmented neutrophils. A smaller population of CD15+CD11b- cells is also observed in bone marrow (FIG. 3 and FIG. 4, region B). This population of CD15+CD11b- cells represents promyelocytes and myelocytes.

Enriched CD34+ cell preparations (post-enrichment, day 0) retain some of the CD15+CD11b+ cells as shown in FIG. 3. However, after three days of culture, a CD15+CD11b- population is observed as shown in FIG. 3. This population of CD15+CD11b- cells increases further by days 7–10 and from days 13–20 a CD15+CD11b+ population is observed. The CD15_CD11b+ population is indicative of the maturation of the cultures to segmented neutrophils. A CD15-CD11b+ population, which is shown in region D of FIG. 4, was observed during days 3–13 of culture but, after the 13th day of culture, this particular population of cells, which represents monocytes or macrophages, was no longer present.

EXAMPLE 4

This example describes a method used to assess the changes in morphology of the cultured CD34+ cells.

The cells that were defined in Example 3, in terms of their expression of CD15 and CD11b, were sorted with a FAC-Star® flow cytometer and their morphology was identified. Approximately 10,000–30,000 cells were sorted into tubes or cytospin funnels. Cytospin slides were prepared by centrifuging the cytospin funnels at 600 rpm for 7 minutes, using a Shandon Cytospin 3 (Pittsburgh, Pa.). The cells were then stained with a Wright-Giemsa stain (Harleco, Gibbstown, N.J.) for 30 seconds. After staining, the cells were rinsed in a phosphate buffer (Sigma) or one minute. The slides were evaluated for the presence of myeloblasts, promyelocytes, myelocytes, metamyelocytes, banded neutrophils, and segmented neutrophils, as well as for the presence of promonocyte and monocytes.

Morphological analysis of CD15 and CD11b sorted fresh bone marrow cells, shown in the left panel of FIG. 4, revealed blast cells and lymphocytes in region A (CD15-CD11b-_, promyelocytes and myelocytes in region B (CD15+CD11b-), metamyelocytes, banded neutrophils, and segmented neutrophils in region C (CD15+CD11b+), and monocytes in region D (CD15-CD11b+). These date are not shown.

Morphological analysis of Wright-Giemsa stained cytospin preparation of CD15 and CD11b sorted CD34+ cells that had been cultured for 7 days, shown in the middle panel of FIG. 4, revealed blast cells, lymphocytes and early promyelocytes in region A (CD15-CD11b-), promyelocytes in region B (CD15+CD11b-), metamyelocytes and banded neutrophils in region C (CD15+CD11b+), and macrophages in region D (CD15-CD11b+). Analysis of region C in sorted cells that had been cultured for 35 days (FIG. 4, right panel) revealed the presence of mature neutrophils. These studies validated the morphological stages observes by flow cytometry and confirmed the sequential expression of CD15 and CD11b during the in vitro differentiation of neutrophils.

EXAMPLE 5

This example describes a colony assay, which is used to determine the types of proliferative cells that are present in the CD34+ cultured cells.

On selected days during the culture of CD34+ cells, aliquots of cells were placed in 35 mm dishes (Nunc) containing methyl cellulose, Iscoves' IMDM (Sigma), 30% FBS (Sigma), 7% Leptalb 7 (Armour Pharmaceuticals, Kankakee, Il.) and the recombinant growth factors rIL-3, rGM-CSF, rG-CSF, rIL-6 and erythropoietin (Amgen) at concentrations of 150 U/ml, 200 U/ml, 150 U/ml, 160 U/ml and 10 U/ml, respectively, to a final concentration of 5–10× $10^3$ cells/ml. Colony assays were set up in triplicate and the colonies (CFU or colony forming unit of about 50 cells or more) were scored as either CFU-GM, CFU-M (colony forming unit—macrophage), BFU-E (burst forming unit—erythroid) or CFU-GEMM.

The number of CFU-GM colonies increased during the early part of the cultures to an average of 4.3 fold after 1 week or 5.6 fold after 2 weeks. Peak increase in CFU-GM occurred around day 10, when the CFU present were predominantly CFU-GM. In contrast, the number of BFU-E generally declined to less than half of the original number by two weeks of culture. Similarly, the numbers of CFU-GEMM and CFU-M also declined.

EXAMPLE 6

This example describes a method used to assess the proliferative potential and colony forming cells present in CD34+ cultured cells.

On selected days (9–14) during the culture of CD34+ cells aliquots of the cells were stained with antibodies that bind to CD15 and CD11b. Cells from the regions described in Example 3 were then sorted into colony assays and into liquid cultures identical to those that had been used before.

Shown in Table II are the results from four proliferate from about 2–5.7 fold after 7 additional days of culture and contain from about 0.4–2% colony forming cells. Cells from region B (CD11b–CD15+) continue to proliferate from about 9.5–12 fold and contain from about 1.1–3% non-erythroid colony forming cells. Colony forming cells are not present in region C and no proliferation takes place upon subsequent culturing. These data indicate that the CD15+ CD11b– cells contain less than about 5% colony forming cells and are capable of proliferating about at least 10 fold.

TABLE II

Proliferation and CFC Present in CD11b/CD15 Phenotypes From Umbilical Cord Blood Enriched CD34+ Cells

| | Experiment Number | | | |
|---|---|---|---|---|
| | 1 | 2 | 3 | 4 |
| % CD34 | 45 | 80 | 80 | 59 |
| Day of Culture | 11 | 14 | 9 | 9 |
| Fold Change Cell # | 72* | 54 | 27 | 34 |
| Region A (11b-15-) fold change | 5.7** | 2 | ND | ND |
| CFU-GM | 19*** | 14 | 8 | 29 |
| CFU-M | 38 | 14 | 25 | 97 |
| BFU-E | 17 | 14 | 39 | 60 |
| CFU-MIX | 0 | 0 | 6 | 22 |
| Cloning Efficiency | 0.55 | 0.42 | 0.78 | 2.08 |
| Region B (11b-15+) fold change | 9.5 | 12 | ND | ND |
| CFU-GM | 41 | 64 | 11 | 27 |
| CFU-M | 69 | 188 | 295 | 246 |
| BFU-E | 0 | 0 | 0 | 0 |
| CFU-MIX | 0 | 0 | 0 | 0 |
| Cloning Efficiency | 1.1 | 2.52 | 3.06 | 2.73 |
| Region C (11b+15+) fold change | 1.1 | ND | ND | ND |

TABLE II-continued

Proliferation and CFC Present in CD11b/CD15 Phenotypes From Umbilical Cord Blood Enriched CD34+ Cells

| | Experiment Number | | | |
|---|---|---|---|---|
| | 1 | 2 | 3 | 4 |
| CFU-GM | 0 | ND | 9 | 0 |
| CFU-M | 0 | ND | 0 | 0 |
| BFU-E | 0 | ND | 0 | 0 |
| CFU-MIX | 0 | ND | 0 | 0 |
| Cloning Efficiency | 0 | 0 | 0.09 | 0 |

ND = not determined
* = Fold increase in cell number during initial culture period
** = Fold increase in cell number from the sorted phenotype after an additional 7 days of culture
*** = Colonies per $10^4$ cells of the sorted phenotype The neutrophil precursor cells may be used in the therapeutic treatment of neutropenia associated with HDC and other types of chemotherapy, such as conventional oncology therapy, neutropenia induced by disease, drugs, toxins, radiation and other agents, genetic neutropenia, and in the treatment of human patients who, although not suffering from severe neutropenia, have reduced populations of neutrophils. The neutrophil precursor cells also may be used in the research of neutrophils, such as neutrophil proliferation and differentiation.

All publications and patent applications cited herein are hereby incorporated by reference to the same extent as if each individual document was individually and specifically indicated to be incorporated by reference.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

EXAMPLE 7

This example describes the proliferation characteristics and differentiation of neutrophil precursors in various combinations of hematopoietic growth factors.

Apheresis samples were collected after peripheral blood counts reached 1000/ul from patients mobilized with G-CSF (10 ug/kg/day) following cyclophosphamide/VP16 chemotherapy. Apheresis was performed using the CS-3000® blood cell separator (Fenwal Division, Baxter Healthcare, Deerfield, Ill.). Bone marrow was collected from normal volunteers. CD34+ cells were isolated using an Isolex® magnetic bead CD34 cell selection system (Baxter Healthcare) or equivalent as described in Example 1. The CD34+ cells were cultured in serum containing media as described in Example 2 to obtain a starting population of CD15+CD11b− neutrophil precursors. The level of proliferation and amount of differentiation into mature granulocytes was then assessed by culturing the neutrophil precursors in various combinations of the hematopoietic growth factors G-CSF, GM-CSF, IL-3, and SCF.

The assays were performed by sorting single cells based upon expression of CD15 and CD11b by flow cytometry into multiwell plates containing 10 ul of culture media with various growth factor combinations. Flow cytometry was performed as described in Example 3. The same studies were performed on fresh bone marrow for comparison.

Plates containing the sorted cells were incubated at 37° C. and the number of cells in each well were counted on days 1, 3 and 10. For further characterization of antigenic expression, cells at varying timepoints of culture were stained with the following antigenic combinations: FITC-CD15/PE-CD11b, FITC-CD71/PE-CD45RA, and FITC-CD67/PE-CD34.

To assess the absolute requirement of growth factors on the proliferation of neutrophil precursors, single cells were plated in the presence or absence of all four growth factors described above. The single cell cultures were incubated for an additional 10 days and then each well was scored for the number of total cells. The wells were categorized according to the number of cells per well. The results are presented below in Table III and show that neutrophil precursors require hematopoietic growth factors to proliferate in culture. Moreover, in the presence of all four growth factors (G-CSF, GM-CSF, IL-3 and SCF) neutrophil precursors are the predominant proliferating phenotype.

TABLE III

Growth Factor Requirement For Neutrophil Precursor Proliferation After 10 Days of Culture

| | | Percent of Total Wells Evaluated | | | | | |
|---|---|---|---|---|---|---|---|
| Phenotype | Growth Factors | 0 Cells/ Well | 1–4 Cells/ Well | 5–8 Cells/ Well | 9–16 Cells/ Well | 17–32 Cells/ Well | >32 Cells/ Well |
| CD15−/CD11b− | All | 92 | 3 | 1 | 0 | 1 | 2 |
| CD15+/CD11b− | All | 68 | 12 | 6 | 4 | 2 | 8 |
| CD15+/CD11b− | None | 95 | 2 | 0 | 0 | 2 | 0 |

To determine which single growth factor or combination of growth factors would support proliferation of neutrophil precursors, various combinations of the above growth factors were tested in the single cell proliferation assay. Shown in Table IV are the results obtained using combinations of G-CSF and GM-CSF together or IL-3 and SCF. What is observed after 10 days in culture in the various growth factor combinations is that the fraction of proliferation neutrophil precursors and the extent of proliferating is higher with the G-CSF/GM-CSF combination compared to either IL-3/SCF or all four factors together.

TABLE IV

Growth Factors Which Support Neutrophil Precursor Proliferation After 10 Days in Culture

| | Percent of Total Wells Evaluated | | | | | |
|---|---|---|---|---|---|---|
| Growth Factors | 0 Cells/ Well | 1–4 Cells/ Well | 5–8 Cells/ Well | 9–16 Cells/ Well | 17–32 Cells/ Well | >32 Cells/ Well |
| ALL FACTORS | 36 | 42 | 3 | 4 | 8 | 7 |
| G-CSF/GM-CSF | 26 | 48 | 6 | 6 | 3 | 10 |
| IL-3/SCF | 39 | 44 | 12 | 4 | 1 | 0 |
| NO FACTORS | 68 | 30 | 1 | 1 | 0 | 0 |

Table V below shows the results obtained on neutrophil precursor proliferation using individual growth factors. These results indicate that G-CSF enhances proliferation to a greater extent then either GM-CSF, IL-3 or SCF alone and to comparable levels as those obtained with the combinations shown above in Table IV.

TABLE V

Individual Growth Factors Which Support Neutrophil Precursor Proliferation After 10 Days in Culture

| | Percent of Total Cells Evaluated | | | | | |
|---|---|---|---|---|---|---|
| Growth Factors | 0 Cells/ Wells | 1–4 Cells/ Well | 5–8 Cells/ Well | 9–16 Cells/ Well | 17–32 Cells/ Well | >32 Cells/ Well |
| G-CSF | 22 | 40 | 10 | 10 | 6 | 13 |
| GM-CSF | 33 | 44 | 12 | 6 | 4 | 1 |
| IL-3 | 20 | 38 | 29 | 10 | 2 | 1 |
| SCF | 25 | 52 | 13 | 8 | 2 | 1 |

What is concluded from the cumulative results shown in Tables III through V is that once neutrophil precursors are obtained using the methods described in Examples 1 through 7, they can be maintained in culture for extended periods of time by culturing in the presence of hematopoietic growth factors. The hematopoietic growth factors shown are the combinations G-CSF, GM-CSF, IL-3 and SCF; G-CSF and GM-CSF; IL-3 and SCF or any of these factors individually. Hematopoietic growth factors other than those described above can also be used. These other growth factors include, for example, IL-6, IL-11, IL-1 and Thrombopoietin, the latter being especially useful if it is desired to differentiate progenitor cells into megakaryocytes. Recombinant fusion proteins containing the active moieties of one or more hematopoietic growth factors can be used as well. For example, PIXY321 (Immunex, Seattle, Wash.) is a fusion protein containing the active moieties of IL-3 and GM-CSF and can also be used to promote the proliferation of neutrophil progenitor cells.

To promote the proliferation of neutrophil precursors, the growth factors need not be the same as the combinations used to obtain the population after the initial period of culture. Thus, growth factors such as G-CSF, for example, can be used alone to supplement the cultures for further proliferation, or, entirely different combinations of growth factors can be used which were not originally present in the original cultures. The above results also indicate that such growth factors which promote the proliferation of neutrophil precursors can be advantageously used therapeutically to augment the treatment of a patient having reduced numbers of neutrophils.

Figure 6:
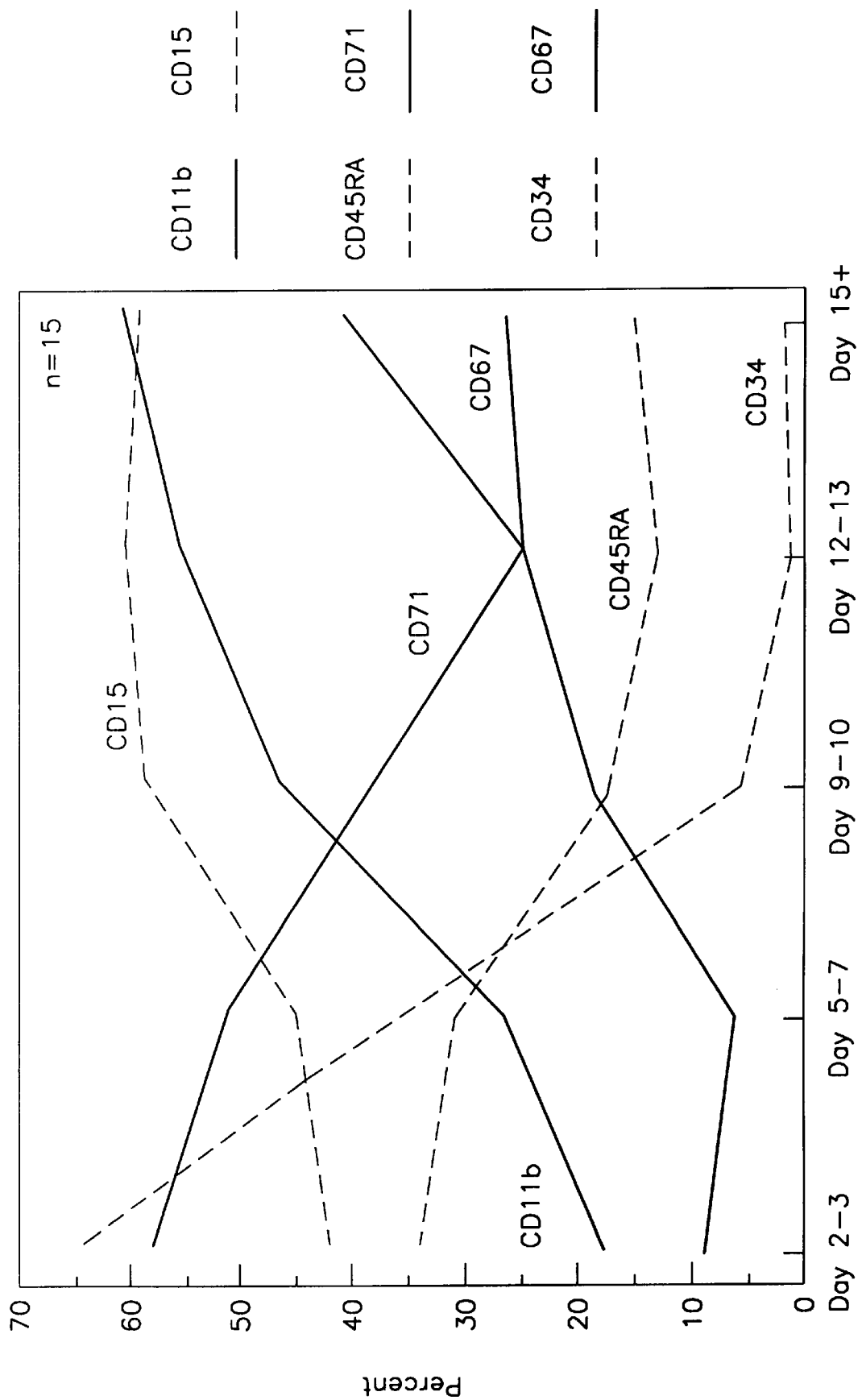
FIG. 6: Antigen expression kinetics of hematopoietic markers on proliferating neutrophil precursor populations.

Other studies were also performed to further characterize the proliferating cultures of neutrophil precursors. For example, comparison between proliferating neutrophil precursor cells obtained from apheresis of peripheral blood or bone marrow samples showed parallel requirements for the growth factor combinations necessary to promote proliferation. Expression of various granulocytic markers were also determined within the proliferating cultures of neutrophil precursor cells (FIG. 6). The results show decreased expression of CD34, CD45RA and CD71 over a period of 2–15 days in culture. Also shown are that the markers to CD15, CD11b and CD67 increase over the same period of time. These latter results indicate that the continued proliferation of neutrophil precursors in culture allows for their differentiation into more mature neutrophils.

We claim:

1. A composition of human neutrophil precursor cells, wherein the cellular component comprises at least 16% myeloblasts and promyelocytes and less than 5% colony forming units, and wherein the cellular component is free of monoclonal antibodies bound thereto.

2. A cell suspension, comprising human neutrophil precursor cells and at least one hematopoietic growth factor, wherein the cellular component comprises at least 16% myeloblasts and promyelocytes and less than 5% colony forming units, and wherein the cellular component is free of monoclonal antibodies bound thereto.

3. An isolated composition of in vitro-cultured human neutrophil precursor cells, wherein the cellular component comprises at least 16% in vitro-cultured myeloblasts and promyelocytes and less than 5% colony forming units.

4. An isolated in vitro-cultured cell suspension, comprising human neutrophil precursor cells and at least one hematopoietic growth factor, wherein the cellular component comprises at least 16% in vitro-cultured myeloblasts and promyelocytes and less than 5% colony forming units.

5. A composition of human neutrophil precursor cells, wherein the cellular component comprises at least 16% CD15+CD11b– neutrophil precursor cells and less than 5% colony forming units, and wherein the cellular component is free of monoclonal antibodies bound thereto.

6. A cell suspension, comprising human neutrophil precursor cells and at least one hematopoietic growth factor, wherein the cellular component comprises at least 16% CD15+CD11b– neutrophil precursor cells and less than 5% colony forming units, and wherein the cellular component is free of monoclonal antibodies bound thereto.

7. An isolated composition of in vitro-cultured human neutrophil precursor cells, wherein the cellular component comprises at least 16% in vitro-cultured CD15+CD11b – neutrophil precursor cells and less than 5% colony forming units.

8. An isolated in vitro-cultured cell suspension, comprising human neutrophil precursor cells and at least one hematopoietic growth factor, wherein the cellular component comprises at least 16% in vitro-cultured CD15+ CD11b– neutrophil precursor cells and less than 5% colony forming units.

9. The composition of either one of claims 1 or 3, wherein said neutrophil precursor cells have the capacity to proliferate and differentiate into segmented neutrophils.

10. The composition of either one of claims 1 or 3, which does not comprise erythroid lineage-committed cells, including BFU-E, when assayed in a colony-forming assay in methylcellulose, in the presence of 10 U/ml erythropoietin.

11. The composition of either one of claims 1 or 3, which additionally comprises one or more cell types selected from the group consisting of myelocytes, metamyelocytes, banded neutrophils, and segmented neutrophils.

12. The composition of either one of claims 1 or 3, wherein said neutrophil precursor cells are derived from neutrophil progenitor cells obtained from a source selected from the group consisting of peripheral blood, bone marrow, and cord blood.

13. The composition of any one of claims 1, 2, 3, or 4, wherein the cellular component comprises 41% myeloblasts and promyelocytes.

14. The composition of any one of claims 1, 2, 3, or 4, wherein the cellular component comprises 45% myeloblasts and promyelocytes.

15. The composition of any one of claims 1, 2, 3, or 4, wherein the cellular component comprises 50% myeloblasts and promyelocytes.

16. The composition of any one of claims 1, 2, 3, or 4, wherein the cellular component comprises 52% myeloblasts and promyelocytes.

17. The composition of any one of claims 1, 2, 3, or 4, wherein the cellular component comprises 58% myeloblasts and promyelocytes.

18. The composition of either one of claims 5 or 7, wherein said CD15+CD11b– cells have the capacity to proliferate and differentiate into segmented neutrophils.

19. The composition of either one of claims 5 or 7, which does not comprise erythroid lineage-committed cells, including BFU-E, when assayed in a colony-forming assay in methylcellulose, in the presence of 10 U/ml erythropoietin.

20. The composition of either one of claims 5 or 7, which additionally comprises one or more cells types selected from the group consisting of myelocytes, metamyelocytes, banded neutrophils segmented neutrophils.

21. The composition of either one of claims 5 or 7, wherein said CD15+CD11b– cells are derived from neutrophil progenitor cells obtained from a source selected from the group consisting of peripheral blood, bone marrow, and cord blood.

22. The composition of any one of claims 5, 6, 7, or 8, wherein the cellular component comprises 41% CD15+ CD11b– neutrophil precursor cells.

23. The composition of any one of claims 5, 6, 7, or 8, wherein the cellular component comprises 45% CD15+ CD11b– neutrophil precursor cells.

24. The composition of any one of claims 5, 6, 7, or 8, wherein the cellular component comprises 50% CD15+ CD11b– neutrophil precursor cells.

25. The composition of any one of claims 5, 6, 7, or 8, wherein the cellular component comprises 52% CD15+ CD11b– neutrophil precursor cells.

26. The composition of any one of claims 5, 6, 7, or 8, wherein the cellular component comprises 58% CD15+ CD11b– neutrophil precursor cells.

27. The cell suspension of either one of claims 6 or 8, wherein said growth factor is selected from the group consisting of G-CSF, GM-CSF, IL-3, SCF, and a recombinant protein containing one or more active moieties of a hematopoietic growth factor.

28. The cell suspension of claim 27, wherein said growth factor is G-CSF.

29. The cell suspension of either one of claims 2 or 4, wherein said growth factor is selected from the group consisting of G-CSF, GM-CSF, IL-3, SCF, and a recombinant protein containing one or more active moieties of a hematopoietic growth factor.

30. The cell suspension of either one of claims 2 or 4, wherein said growth factor is G-CSF.

* * * * *

UNITED STATES PATENT AND TRADEMARK OFFICE
CERTIFICATE OF CORRECTION

PATENT NO.    : 5,955,357
DATED         : September 21, 1999
INVENTOR(S)   : Bender et al.

It is certified that error appears in the above-identified patent and that said Letters Patent is hereby corrected as shown below:

Column 3,
Line 18, please delete "an," and replace with -- and --.
Line 55, please delete "cells," and replace with -- cells. --.

Column 4,
Line 1, please delete "myelocyte," and replace with -- myelocytes, --.
Line 58, please delete "form" and replace with -- from --.

Column 5,
Line 11, please delete "or combination" and replace with -- or in combination --.
Line 16, please delete "form" and replace with -- from --.

Column 6,
Line 51, please delete "form" and replace with -- from --.
Line 54, please delete "form" and replace with -- from --.

Column 7,
Line 50, please delete "form" and replace with -- from --.

Column 8,
Line 31, please delete "form" and replace with -- from --.
Line 62, please delete "from" and replace with -- form --.
Line 65, please delete "from" and replace with -- form --.

Column 9,
Line 1, please delete "minimize" and replace with -- minimized --.
Line 66, please delete "cell" and replace with -- cells --.

Column 10,
Line 66, please delete "from" and replace with -- form --.

Column 11,
Lines 3 through 7, please delete "Alternatively, the cellular component of the composition cellular component is comprised of at least about 16% myeloblasts and promyelocytes and less than about 5% colony forming units (CFU) of at least about 50 cells. --.
Line 18, please delete "metamylocytes," and replace with -- metamyelocytes, --.
Line 66, please delete "linage-uncommitted" and replace with
-- lineage-uncommitted --.

UNITED STATES PATENT AND TRADEMARK OFFICE
CERTIFICATE OF CORRECTION

PATENT NO. : 5,955,357
DATED : September 21, 1999
INVENTOR(S) : Bender et al.

It is certified that error appears in the above-identified patent and that said Letters Patent is hereby corrected as shown below:

Column 12,
Line 30, please delete "patent" and replace with -- patient --.
Line 46, please delete "and initial" and replace with -- an initial --.

Column 13,
Line 29, please delete "In additions," and replace with -- In addition, --.

Column 15,
Line 35, please delete "an" and replace with -- and --.
Line 55, please delete "wvidenced" and replace with -- evidenced --.
Line 62, please delete "late" and replace with -- plate --.

Column 16,
Line 37, please delete "(Sigma) or" and replace with -- (Sigma) for --.
Line 45, please delete "CD11b-_," and replace with -- CD11b-), --.
Line 48, please delete "date" and replace with -- data --.
Line 60, please delete "observes" and replace with -- observed --.

Column 17,
Line 33, please delete "proliferate" and replace with -- experiments. Cells from region A (CD11b-CD15-) continue to proliferate --.

Column 18,
Line 57, please delete "CD15+CD11b" and replace with -- $CD15^+CD11b$ --.

Signed and Sealed this

Tenth Day of September, 2002

*Attest:*

JAMES E. ROGAN
*Attesting Officer*   *Director of the United States Patent and Trademark Office*